| United States Patent [19] | [11] Patent Number: 4,617,297 |
| --- | --- |
| Boris et al. | [45] Date of Patent: Oct. 14, 1986 |

[54] METHOD OF TREATING DISEASE STATES BY THE ADMINISTRATION OF 1α,25,26-TRIHYDROXYCHOLECAL-CIFEROL

[75] Inventors: Alfred Boris, Parsippany; John J. Partridge; Milan R. Uskokovic, both of Upper Montclair, all of N.J.

[73] Assignee: Hoffmann-La Roche Inc., Nutley, N.J.

[21] Appl. No.: 596,325

[22] Filed: Apr. 3, 1984

Related U.S. Application Data

[63] Continuation of Ser. No. 458,224, Jan. 14, 1983, abandoned, which is a continuation-in-part of Ser. No. 348,389, Feb. 12, 1982, abandoned.

[51] Int. Cl.$^4$ .................... A01N 45/00; A61K 31/59
[52] U.S. Cl. ................................. 514/167; 260/397.1; 260/397.4; 260/397.2
[58] Field of Search .................... 424/236; 260/397.2, 260/397.1, 239.55 D; 514/167

[56] References Cited

U.S. PATENT DOCUMENTS

| 4,195,027 | 3/1980 | DeLuca et al. | 260/397.2 |
| 4,204,995 | 5/1980 | Barner et al. | 260/397.2 |
| 4,407,754 | 10/1983 | Barner et al. | 260/239.55 D |

OTHER PUBLICATIONS

Arch. Biochem. Biophys., 210, (1981), article by Tanoka et al, pp. 104–109.
Helv. Chim. Acta (64) (1981) article by Patridge et al., pp. 2138–2141.

*Primary Examiner*—Elbert L. Roberts
*Attorney, Agent, or Firm*—Jon S. Saxe; Bernard S. Leon; Matthew Boxer

[57] ABSTRACT

The present invention relates to the method of treating disease states characterized by higher than normal levels of endogenously produced 1α,25 dihydroxy-cholecalciferol or conditions where there is an increased sensitivity to 1α, 25 dihydroxy-cholecalciferol by administering to an organism suffering from such a disease state a pharmaceutically effective amount of the R or S epimer of 1α,25,26 trihydroxy-cholecalciferol.

12 Claims, No Drawings

METHOD OF TREATING DISEASE STATES BY THE ADMINISTRATION OF 1α,25,26-TRIHYDROXYCHOLECALCIFEROL

RELATED APPLICATION

This is a continuation, of application Ser. No. 458,224 filed Jan. 14, 1983, now abandoned which in turn is a continuation-in-part of patent application Ser. No. 348,389 Feb. 12, 1982, now abandoned.

BACKGROUND OF THE INVENTION

This invention relates to a process for the preparation of 1α,25S,26-trihydroxycholecalciferol and the analog 1α,25R,26-trihydroxycholecalciferol and the use thereof by treatment of disease states characterized by higher than normal serum levels of 1,25(OH)$_2$D$_3$.

Vitamin D$_3$ is a well-known agent for the control of calcium and phosphorous homeostasis. In the normal animal or human, this compound is known to stimulate intestinal calcium transport and bone-calcium mobilization and is effective in preventing rickets.

It is also now well known that to be effective, vitamin D$_3$ must be converted in vivo to its hydroxylated forms. For example, the vitamin is first hydroxylated in the liver to form 25-hydroxy-vitamin D$_3$ and is further hydroxylated in the kidney to produce 1α,25-dihydroxy vitamin D$_3$ or 24,25-dihydroxy vitamin D$_3$. The 1α,25-dihydroxylated form of the vitamin is generally considered to be the physiologically-active or hormonal form of the vitamin and to be responsible for what are termed the vitamin D-like activities such as increasing intestinal absorption of calcium and phosphate, mobilizing bone mineral and retaining calcium in the kidneys.

Since the discovery of biologically-active metabolites of vitamin D$_3$, there has been much interest in the preparation of structural analogs of these metabolites because such compounds may represent useful therapeutic agents for the treatment of diseases resulting from calcium metabolism disorders. Specifically included among the disease states for which the compound of formula I is indicated are hypercalcemia, sarcoidosis, hypercalciuria, nephrolithiasis, nephrocalcinosis and other disease states which are characterized by higher-than-normal levels of the active vitamin D$_3$ metabolite, 1α,25-dihydroxycholecalciferol. The R and S epimers of 1,25,26-trihydroxycholecalciferol lower the serum level of 1,25-dihydroxycholecalciferol. Both the R and S epimers promote bone mineralization in vitamin D-deficient animals. The R epimer promotes bone mineralization in disodium-ethane-1-hydroxy-1,1-diphosphonate-blocked animals.

SUMMARY OF THE INVENTION

A process and intermediates for preparing 1α,25S,26-trihydroxycholecalciferol 1α,25R,26-trihydroxycholecalciferol and the R,S mixtures of the epimers from the readily-available 1α,3β-dihydroxyandrost-5-en-17-one which is made by a known microbiological process from 3β-hydroxyandrost-5-en-17-one [R. M. Dodson, A. H. Goldkamp and R. D. Muir, J.Amer.-Chem. Soc., 82 4026 (1960], is described.

The present invention relates to the method of treating disease states characterized by higher than normal levels of endogenously produced 1α,25 dihydroxycholecalciferol or conditions where there is an increased sensitivity to 1α,25 dihydroxycholecalciferol by administering to a host suffering from such a disease state a pharmaceutically effective amount of the R or S epimer of 1α25,26 trihydroxycholecalciferol.

DETAILED DESCRIPTION OF THE INVENTION

As used throughout the specification and the appended claims, the term "lower alkyl" refers to a monovalent substituent consisting solely of carbon and hydrogen of from 1 to 8 carbon atoms which may be straight- or branched-chain. Examples of lower alkyl groups are methyl, ethyl, n-propyl, i-propyl, tert.butyl, hexyl, heptyl, octyl and so forth. The term "lower alkylene" refers to a divalent substituent consisting solely of carbon and hydrogen of from 1 to 8 carbon atoms which may be straight- or branched chain and whose free valences are attached to two distinct groups. Examples of alkylene groups are methylene, ethylene, propylene, butylene, amylene, hexylene, heptylene, octylene and the like. The term "lower alkoxy" refers to a lower alkyl group attached to the remainder of the molecule of oxygen. Examples of alkoxy groups are methoxy, ethoxy, isopropoxy, tert.butoxy and so forth. The term "phenyl alkoxy" refers to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic acid formed by removal of the hydrogen from the hydroxyl portion of the carboxyl group. Examples of alkanoyloxy groups are formyloxy, acetoxy, butyryloxy, hexanoyloxy and so forth. The term "substituted" as applied to "phenyl" refers to phenyl which is substituted with one or more of the following groups: alkyl, halogen (i.e., fluorine, chlorine, bromine or iodine), nitro, cyano, trifluoromethyl and so forth. The term "alkanol" refers to a compound derived by protonation of the oxygen atom of an alkoxy group. Examples of alkanols are methanol, ethanol, 2-propanol, 2-methyl-2-propanol and the like.

In the formulas presented herein, the various substituents are illustrated as joined to the steroid nucleus by one of these notations: a solid line (━) indicating a substituent which is in the ≡-orientation (i.e., above the plane of the molecule), a dotted line ( - - - ) indicating a substituent which is in the α-orientation (i.e., below the plane of the molecule) or a wavy line (∼∼∼) indicating a substituent which may be in the ≡- or ≡- orientation. The formulas have all been drawn to show the compounds in their absolute stereochemical configurations. Since the starting materials are derived from a naturally-occurring steroid, the products exist in the single absolute configuration depicted herein. However, the processes of the present invention are intended to apply as well to the synthesis of steroids of the "unnatural" and racemic series, i.e., the epimers of the compounds depicted herein and mixtures of both. Thus, one may begin the synthesis utilizing "unnatural" or racemic starting materials to prepare "unnatural" or racemic products, respectively.

The Greek letter xi (ξ) in the name of a vitamin D$_3$ intermediate or metabolite indicates that the stereochemistry of the substituent to which it refers is undefined or that the product consists of a mixture of compounds epimeric at the designated position.

The nomenclature adopted to define absolute configuration of substituents bound to carbon atom 25 of the steroid nucleus is described in the Journal of Organic Chemistry, 34 (1970) 2849 under the title "TUPAC Tentative Rules for the Nomenclature of Organic Chemistry. Section E. Fundamental Stereochemistry".

In the process of the present invention, 1α,25R,26-trihydroxycholecalciferol, 1α,25S,26-trihydroxycholecalciferol and the 25R,S mixture of its epimers of the formula

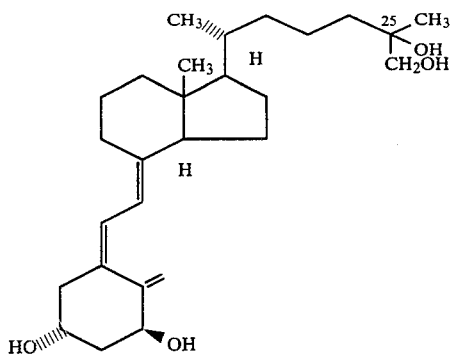

wherein the absolute configuration at C-25 is R or S or an R,S mixture, are prepared by the removal of a ketal protecting group from the immediate acetonide precursor of the formula

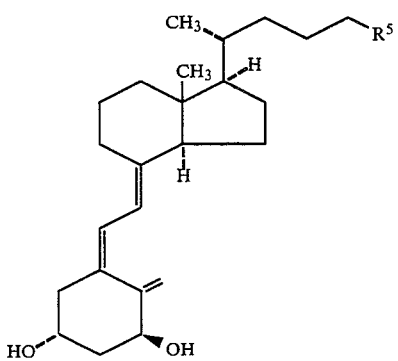

wherein $R^5$ is a group of the formula

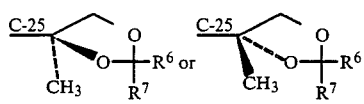

wherein $R^6$ and $R^7$ are lower alkyl or taken together are lower alkylene; absolute configuration at C-25 is R or S or an RS mixture.

Within the scope of the present invention are compounds of the formula

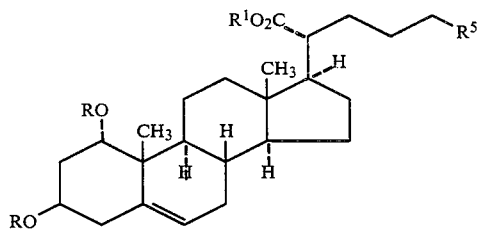

wherein R is a group of the formula

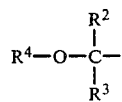

wherein $R^2$ is hydrogen or lower alkyl; $R^3$ and $R^4$ each taken independently are lower alkyl and $R^3$ and $R^4$ taken together are lower alkylene of from 3 to 6 carbon atoms; $R^1$ is lower alkyl, phenyl or substituted phenyl; $R^5$, $R^6$ and $R^7$ are as above.

The starting material in the process of the present invention is a pregn-5-en-21-oic acid ester of the formula

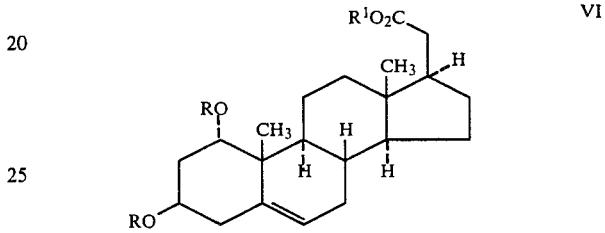

wherein R and $R^1$ are as above.

The compound of formula VI may be prepared according to the following methodology starting with the known 1α,3β-dihydroxyandrost-5-en-17-one [R. M. Dodson, A. H. Goldkamp and R. D. Muir, J. Amer. Chem. Soc., 82 4026 (1960)].

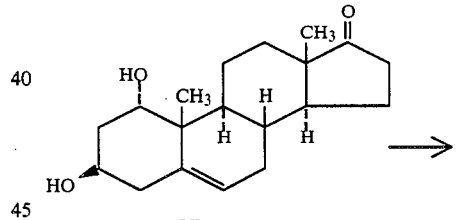

VI-A

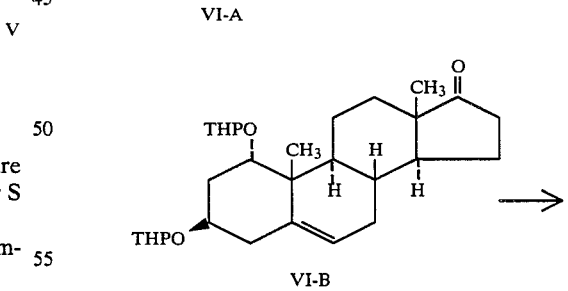

VI-B

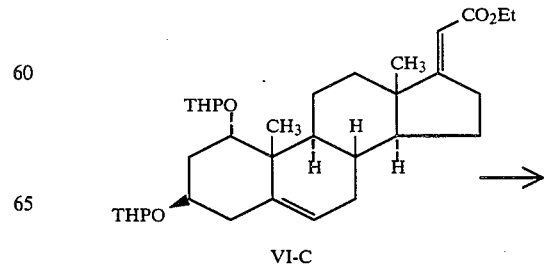

VI-C

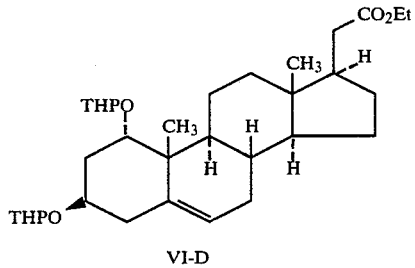

VI-D

The 1α,3β-dihydroxyandrost-5-en-17-one (formula VI-A) was stirred with 3,4-dihydro-2H-pyran and p-toluenesulfonic acid to yield ketone (formula VI-B). This substance was treated with triethylphosphonoacetate and ethanolic sodium ethoxide to yield the unsaturated ester (formula VI-C). Catalytic hydrogenation of formula VI-C over platinum oxide catalyst then afforded [1α,3β]-1,3-bis[(tetrahydro-2H-pyran-2-yl)oxy]pregn-5-en-21-oic acid ethyl ester (formula VI-D) which corresponds to compounds of the formula VI. The sequence (formula VI-A-formula VI-D) parallels the work of J. Wicha and K. Bal, J.Chem.Soc.Perkin Trans. I (1978) 1282.

In the process of the present invention, the pregn-5-en-21-oic acid ester of the formula

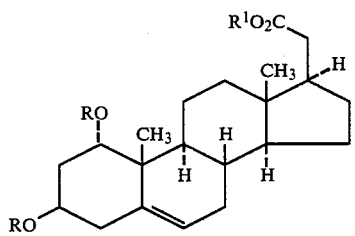

VI wherein R and R¹ are as above, is treated with an appropriate organometallic reagent so as to yield a metallated pregn-5-en-21-oic acid ester of the formula

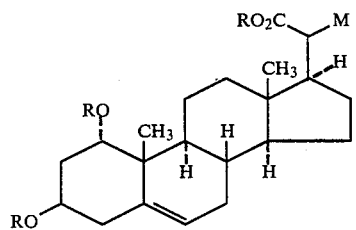

VII wherein R and R¹ are as above and M is lithium, sodium, potassium, magnesium/2 or zinc/2.

For example, the lithium salt may be formed by reaction of the compound of formula VI with, for example, lithium diisopropylamide. The sodium salt may be formed by reaction of the compound of formula VI with, for example, sodium hexamethyldisilazane. The potassium salt may be formed by reaction with the compound of formula VI with, for example, potassium hydride.

The metallated pregn-5-en-21-oic acid ester of formula VII is preferably generated in situ and is then reacted with a compound of the formula

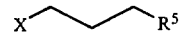

VIII wherein X is iodo, bromo, chloro, lower alkyl sulfonyloxy, phenylsulfonyloxy or substituted phenylsulfonyloxy; and R⁵ is a group of the formula

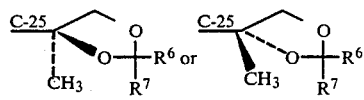

V wherein R⁶ and R⁷ are lower alkyl or taken together are lower alkylene; and the absolute configuration at C-25 is R or S or an R,S mixture, according to the method of J. Wicha and K. Bal, J.Chem.Soc.Perkin Trans. I (1978) 1282 so as to yield the alkylated compound of the formula

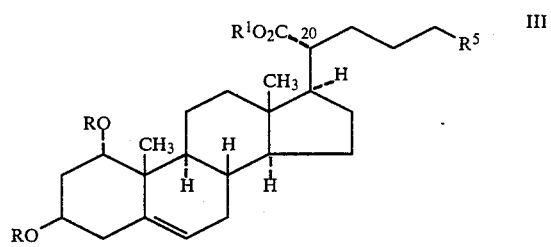

III wherein R, R¹ and R⁵ are as above; and the absolute configuration at the C-25 position is R or S or an R,S mixture.

The aforementioned reaction sequence starting with the compound of formula VI may be carried out in aprotic inert solvents such as, for example, ethers. e.g., diethyl ether, tetrahydrofuran, dimethoxyethane, dioxane and so forth; amides, e.g., hexamethylphosphoramide and so forth. Preferred solvents for this purpose are tetrahydrofuran and hexamethylphosphoramide. The use of tetrahydrofuran-hexamethylphosphoramide mixtures is particularly preferred.

The alkylation reactions between compounds of formulas VII and VIII are conveniently carried out at a temperature between −78° C. and 60° C. Most preferably, the alkylation reaction is conducted between a temperature of about −40° C. to 0° C. The desired alkylation product of formula III, containing the desired 20R-absolute configuration, can be isolated by the usual chemical and physical means such as chromatography and in this manner can be separated from any undesired impurities such as materials of formula VI and VIII.

The compound of formula VIII may be prepared according to the method described in J. J. Partridge, S. J. Shiuey, N. K. Chadka, E. G. Baggiolini, J. F. Blount and M. R. Uskokovic, J. Amer. Chem. Soc. 103 1253 (1981).

In the next step, the compound of formula III is reduced to a compound of the formula

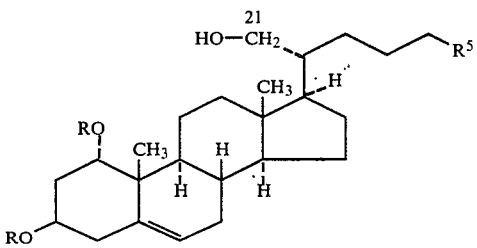

wherein R and R⁵ are as above, and the absolute configuration at the C-25 position is R or S or an R,S mixture, by reduction of the R¹ ester grouping of formula III with a complex metal hydride reducing agent. Suitable complex metal hydride reducing agents for this purpose include alkali metal aluminum hydrides such as lithium aluminum hydride; mono-, di- or tri(lower alkoxy) alkali metal aluminum hydrides such as, for example, lithium tris(tert.butoxy) aluminum hydride; mono-, di- or tri(lower alkoxy lower alkoxy) alkali metal aluminum hydrides such as, for example, sodium bis(2-methoxyethoxy) aluminum hydride; di(lower alkyl) aluminum hydrides such as, for example, diisobutyl aluminum hydride; and so forth. A particularly-preferred complex metal reducing agent for this purpose is lithium aluminum hydride. Suitable solvents for this reduction include ethers such as diethyl ether, tetrahydrofuran, dimethoxyethane and dioxane. The reduction is conveniently carried out at a temperature between about 0° C. and 100° C., most preferably between about 35° C. and 70° C.

The C-21 alcohol of formula IX is converted in the next step to a C-21 halide or sulfonate ester of the formula

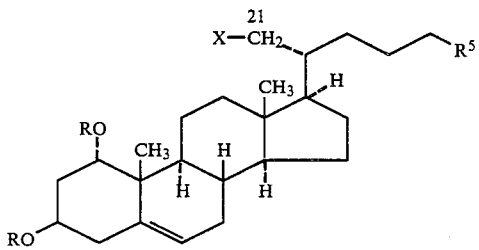

wherein R, R⁵ and X are as above; and the absolute configuration at the C-25 position is R or S or an R,S mixture.

The compound wherein X is p-toluene sulfonyloxy is especially preferred.

To prepare a compound wherein the C-21 substituent is a substituted sulfonyloxy group, one would react the previously-mentioned C-21 alcohol of formula IX with a properly-substituted sulfonyl halide in the presence of a base according to methods known in the art. The preparation of compounds wherein the C-21 substituent is iodo, bromo or chloro can be accomplished either by direct conversion of the C-21 alcohol of formula IX to the desired halo group by means of a halogenating agent such as, for example, phosphorus tribromide, according to methods well known in the art or by reaction of one of the C-21 sulfonate esters with a halide ion containing compound. For example, the C-21 sulfonate ester compound where the ester substituent is tosyloxy may be reacted with an alkali metal bromide or iodide, for example, potassium bromide or potassium iodide, to afford the C-21 halide compound where the halide is bromo or iodo, respectively. All of these interconversions to prepare the C-21 halide and C-21 sulfonate ester compounds are standard in the art for the preparation of primary alkyl halides and sulfonate esters from primary alcohols.

In the next step, the C-21 halide or sulfonate ester of formula X is converted to a compound of the formula

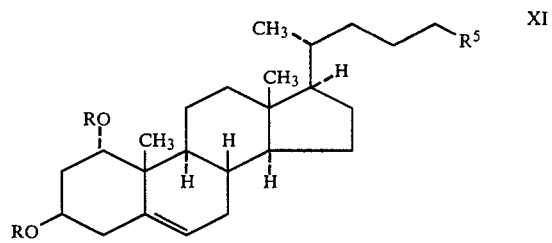

wherein R and R⁵ are as above; and the absolute configuration at the C-25 position is R or S or an R,S mixture, by reaction with a complex metal hydride reducing agent.

Suitable complex metal hydride reducing agents for this purpose include metal aluminum hydrides such as lithium aluminum hydride; mono-, di- or tri(lower alkoxy) alkali metal aluminum hydride such as, for example, lithium tri(tert.butoxy) aluminum hydride; mono-, di- or tri(lower alkoxy lower alkoxy) aluminum metal hydrides such as, for example, sodium bis(2-methoxyethoxy) aluminum hydride; di(lower alkyl) aluminum hydrides such as, for example, diisobutyl aluminum hydride; and so forth. A particularly-preferred complex metal hydride reducing agent for this purpose is lithium aluminum hydride. Suitable solvents for the reduction include ethers such as diethyl ether, tetrahydrofuran, dimethoxyethane and dioxane. The reduction is normally carried out at a temperature between about room temperature and about 100° C., most preferably between about 35° C. and 70° C. Other suitable reducing agents, particularly when the C-21 halide is iodo or bromo, are alkali metal cyanoborohydrides such as, for example, sodium cyanoborohydride (sodium cyanotrihydroborate); tri(lower alkyl) tin hydrides such as tri-n-butyltin hydride; and tri(aryl) tin hydrides such as triphenyltin hydride; and so forth. A particularly-preferred complex metal reducing agent is tri-n-butyltin hydride. Suitable solvents for the reduction include ethers such as diethyl ether, tetrahydrofuran, dimethoxyethane and dioxane. The reduction is normally carried out at a temperature between about −20° C. and 80° C., most preferably between about 0° C. and 40° C.

In the next step, the compound of formula XI is selectively deprotected by removal of the tetrahydropyranyl protecting groups at the 1 and 3 positions of the steroid molecule with a strong acid in a protic solvent—ketal solvent mixture—so as to yield a compound of the formula

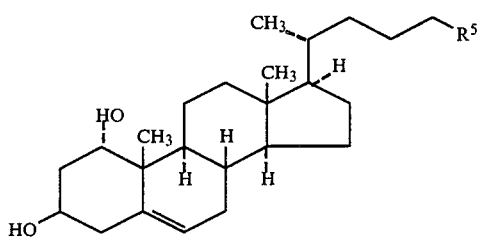

XII wherein $R^5$ is as above; and the absolute configuration at the C-25 position is R or S or an R,S mixture.

Suitable strong acids for this purpose include mineral acids such as hydrochloric or sulfuric acid; and organic sulfonic acids such as p-toluenesulfonic acid. Suitable protic solvents include alcohols such as methanol and ethanol. Suitable ketal solvents include 2,2-dimethoxypropane and 2,2-diethoxypropane. It is preferable to carry out the removal of the aforementioned protecting groups at a temperature between about $-10°$ C. and about 80° C., most preferably between about 0° C. and 40° C.

The 1,3-diol compound of formula XII is then alkanoylated to the $1\alpha,3\beta$-dialkanoylated compound of the formula

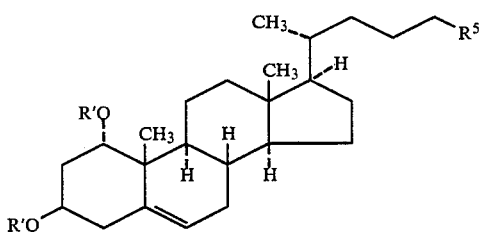

XIII wherein R' is lower alkanoyl; $R^5$ is as above; and the absolute configuration at the C-25 position is R or S or an R,S mixture, by methods well known in the art. For example, to acylate the $1\alpha$- and $3\beta$-hydroxy groups of compound XIII, one may employ an acylating agent such as acetic anhydride and pyridine at temperatures in the range of about 25° C. to about 100° C. and a trace of 4-dimethyl amino pyridine catalyst.

The $1\alpha,3\beta$-dialkanoylated compound of formula XIII is next allylically halogenated to a mixture of $1\alpha,3\beta$-dialkanoyl,$7\alpha$- and $7\beta$-halocholesterols of the formula

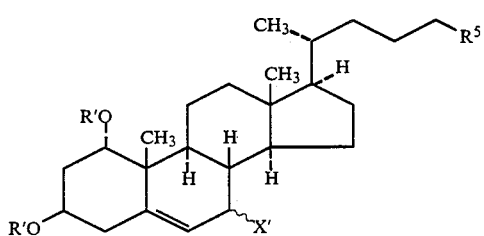

XIV wherein R' and $R^5$ are as above; X' is iodo, bromo or chloro; and the absolute configuration at the C-25 position is R or S or an R,S mixture.

The halogenation reaction is accomplished using a suitable halogenation agent such as 1,3-dibromo-5,5-dimethylhydantoin, N-chlorosuccinimide, N-bromosuccinimide, N-bromoacetamide and the like dissolved in a saturated aliphatic hydrocarbon or halocarbon such as hexane or carbon tetrachloride in the presence of an acid scavenger such as sodium bicarbonate or sodium carbonate at the boiling point of the reaction medium to give a mixture of $1\alpha,3\beta$-dialkanoyl,$7\alpha$- and $7\beta$-halocholesterol which is used in the following dehydrohalogenation step without separation of the $7\alpha$-halo-isomer from the $7\beta$-isomer.

The $1\alpha,3\beta$-dialkanoyl,$7\alpha$- and $7\beta$-halocholesterol mixture of formula XIV is converted to the steroid 5,7-diene of the formula

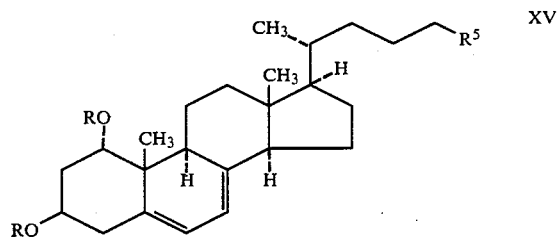

XV wherein R' and $R^5$ as are above; and the absolute configuration at the C-25 position is R or S or an R,S mixture, by a dehydrohalogenation step. The dehydrohalogenation of the crude mixture of $1\alpha,3\beta$-dialkanoyl,$7\alpha$- and $7\beta$-halocholesterol is effected by heteroaromatic and aliphatic tertiary amines, pyridines and alkylated pyridines such as picolines, lutidines and collidines; suitable aliphatic tertiary amines are triethylamine, tripropylamine, 1,5-diazabicyclo(4.3.0) non-5-ene, 1,4-diazabicyclo(2.2.2)octane and the like; s-collidine being preferred. Trialkylphosphites are also useful in the dehydrohalogenation step. Suitable inert organic solvents include aromatic and aliphatic organic solvents such as benzene, toluene, xylene, decalin and the like. Xylene is the preferred solvent. The reaction proceeds readily at temperatures from about 50° C. to the reflux temperature of the reaction medium, most readily at the reflux temperature of the solvent system. The desired steroid 5,7-diene of formula XV can be isolated by the usual chemical and physical means such as chromatography and in this manner can be separated from any undesired impurities.

In the next step, the steroid 5,7-diene of formula XV is converted into the protected precholecalciferol compound of the formula

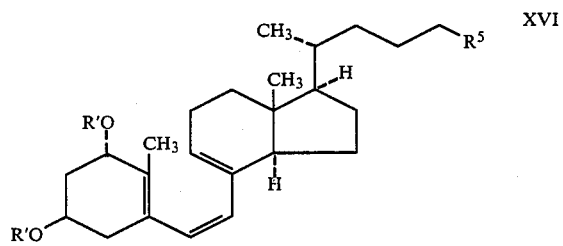

XVI wherein R' and $R^5$ are as above; and the absolute configuration at the C-25 position is R or S or an R,S mixture, by irradiation under an inert atmosphere by means of a mercury lamp equipped with a glass cooling finger at a temperature of about $-40°$ C. to about 25° C., $-5°$ C. being the preferred irradiation temperature for the period of time necessary to effect about 50% conversion of the starting material. Suitable inert atmospheres include nitrogen, helium, argon and the like. Suitable source of irradiation energy include high- and low-pressure mercury, xenon-mercury and thallium-mercury lamps. High-pressure mercury lamps are preferred. A 450 W Hanovia high-pressure mercury lamp is the most preferred source of irradiation energy. Suitable inert organic solvent systems for the irradiation include mixtures of saturated aliphatic hydrocarbons such as pentane, hexane, iso octene and the like and ethereal solvents such as diethyl ether, dimethoxyethane, tetrahydrofuran, dioxane and the like. Preferred mixtures contain hexane and tetrahydrofuran.

Upon completion of the irradiation, the solvents are removed by evaporation, and the residue is separated into the pure protected 1α,3β-dialkanoyl precholecalciferol of formula XVI and pure unchanged steroid 5,7-diene of formula XV on a high-performance liquid chromatography column using a solid absorbent and an inert organic eluant. Suitable organic eluents for the separation step include mixtures of hydrocarbons such as n-hexane, isooctane, cyclohexane and the like and esters such as ethyl acetate, ethyl formate and the like. Suitable solid absorbents include Porasil, Corasil, Biosil, Zorbax, Zorbax-Sil, Sil-X kand the like. A Waters Associates Chromatograph Model 202 using an four-foot by 1-inch Porasil A column and a mixture of n-hexane ethyl acetate as the eluant is the preferred high-performance liquid chromatographic system.

Unchanged, 5,7-diene of formula XV is recycled through the irradiation process to obtain additional quantities of pure protected 1α,3β-dialkanoyl precholecalciferol of formula XVI thereby rendering this crucial step of the process and the overall process highly efficient in comparison with related processes previously disclosed, for example, by D. H. R. Barton et al., J. Chem. Soc. Chem. Comm. (1974) 203 and by H. F. DeLuca et al. Tetrahedron Lett. (1972) 4417. Alternatively, the steroid 5,7-diene of formula XV is converted into the protected precholecalciferol of formula XVI by the process disclosed in British Patent Specification 1,592,170 published July 1, 1981.

The protected 1α,3β-dialkanoyl precholecalciferol of formula XVI is saponified to the precholecalciferol of the formula

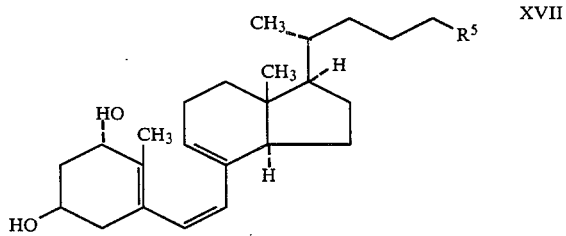

XVII wherein $R^5$ is as above; and the absolute configuration at C-25 is R or S or an R, S mixture.

The saponification of the compound of formula XVII is conducted by treatment with strong bases in protic solvents. Suitable bases include alkali and alkaline earth hydroxides, alkoxides such as methoxides, ethoxides and the like. Potassium hydroxide is most preferred. Suitable solvents include alcohols such as methanol and ethanol and water containing a miscible cosolvent to help solubilize the organic reactants, for example, an ether such as tetrahydrofuran or dimethoxyethane. Methanol is most preferred. It is preferable to carry out the removal of the alkanoyl protecting groups R of formula XVI at a temperature between about −20° C. and about 60° C., most preferably between about −5°
C. and 30° C. It is also preferable to perform the saponification under an inert atmosphere of nitrogen, argon and the like.

The next step in the sequence involves the thermal isomerization of precholecalciferol of formula XVII to the cholecalciferol of the formula

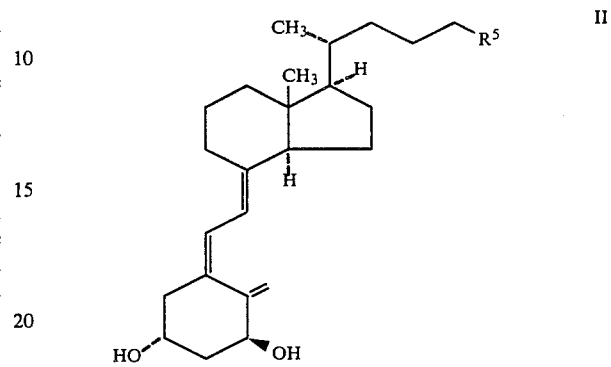

II wherein $R^5$ is as above; and the absolute configuration at the C-25 position is R or S, or S,R-mixture by heating the precholecalciferol of formula XVII in an inert solvent such as the ethers, dioxane, tetrahydrofuran, dimethoxyethane and the like; the aromatic hydrocarbons such as benzene, toluene and the like under an inert atmosphere such as argon, helium and the like by methods well known in the art. See, for example, D. H. R. Barton et al., J. Amer. Chem. Soc. 98 (1973) 2748.

The final step in the sequence involves the removal of the ketal protecting group of the cholecalciferol of formula II to give 1α,25,26-trihydroxycholecalciferol of the formula

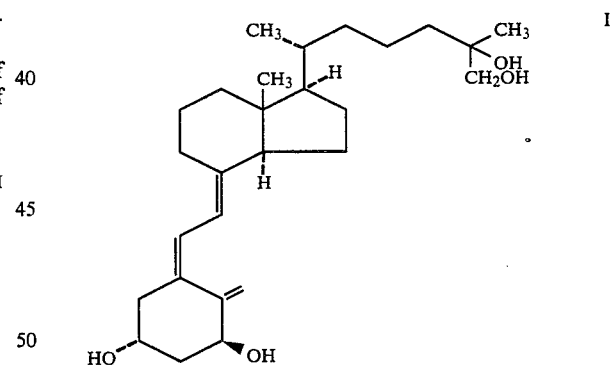

I wherein the absolute configuration at C-25 is R or S or an R,S mixture, by treatment with an acid in a protic solvent. Suitable acids include mineral acids such as hydrochloric or sulfuric acid and the like, organic acids such as p-toluenesulfonic acid, trifluoroacetic acid and the like, and cationic exchange resins in the hydrogen form such as Bio-Rad AG 50W-X4, Bio-Rad AG 50W, Dowex 50W, Duolite C20, Amberlite 1R and the like. Cationic exchange resins in the hydrogen form are preferred. Bio-Rad 50W-X4 is most preferred. Suitable protic solvents include the alkanols, methanol, ethanol, 2-propanol and the like, and alkandiols such as ethylene glycol, propylene glycol and the like, and water mixed with a miscible cosolvent to help solubilize the organic reactants, for example, ethers such as tetrahydrofuran or dimethoxyethane; or a ketone such as acetone. Alkanols are preferred, methanol is most preferred. It is preferable to carry out the removal of the ketal protecting group at a temperature between about $-10°$ C. and about 80° C., most preferably between about 0° C. and 40° C.

The R and S-epimers of the compound of formula I lower the serum level of $1\alpha,25$-dihydroxycholecalciferol. Additionally, both the R and S-epimers promote bone mineralization in Vitamin D-deficient animals, but only the R-epimer promotes bone mineralization in disodium-ethane-1-hydroxy-1,1-diphosphonate-blocked animals. The R and S-epimers are useful for the treatment of disease states which are characterized by higher-than-normal serum levels of the endogenously-produced active vitamin $D_3$ metabolite, $1\alpha,25$-dihydroxycholecalciferol, or in conditions in which there is an increased sensitivity to $1\alpha,25$-dihydroxycholecalciferol.

The foregoing activities can be demonstrated in the following tests:

$1\alpha,25(S),26$-trihydroxycholecalciferol and $1\alpha,25(R),26$-trihydroxycholecalciferol were tested for (a) anti-rachitogenc activity, (b) intestinal calcium absorption activity (c) prevention of disodium ethane-1-hydroxy-1,1-diphosphonate induced mineralization block and (d) the effects of administration of $1\alpha,25(S),26$-trihydroxycholecalciferol and $1\alpha,25(R),26$-trihydroxycholecalciferol on the serum level of $1\alpha,25$-dihydroxy cholecalciferol, and 25-hydroxycholecalciferol.

(a) Anti-Rachitogenic Activity in Chicks

One-day-old White Leghorn cockerels are placed on a vitamin D-defidient diet which contains 1% calcium and 0.7% phosphorus and are housed under ultraviolet-free lighting (General Electric F40G0 gold fluorescent lights). Compounds are dissolved in propylene glycol and administered orally in a volume of 0.2 ml for 21 consecutive days to chicks which are one to two days of age at the start of treatment. Controls are treated with vehicle alone. Compounds are prepared in amber flasks and the solutions are flushed with argon and refrigerated after each dosing period. Chicks are autopsied on the day after the last treatment day. Blood is collected for determination of serum calcium and phosphorus and tibia dry weight and ash weight are determined. Usually, ten chicks are used for each treatment group and for the control group. The results of the anti-rachitogenic activity assay are in Table I. The results show that the R and S-epimers of $1\alpha,25,26(OH)_3D_3$ possess similar antirachitogenic activity.

TABLE I

ANTI-RACHITOGENIC ACTIVITIES OF $1,25S,26(OH)_3D_3$ AND $1,25R,26(OH)_3D_3$ IN CHICKS

| DOSE NG/CHICK/DAY | MEAN TIBIA ASH WEIGHT (MG) = S.E. | |
|---|---|---|
| | $1,25S,26(OH)_3D_3$ | $1,25R,26(OH)_3D_3$ |
| 0 | 112.1 ± 6.2 | |
| 30 | 124.9 ± 2.8 NS | 122.6 ± 4.1 NS |
| 100 | 159.4 ± 4.4*** | 157.5 ± 5.3*** |
| 300 | 187.0 ± 8.7*** | 207.8 ± 7.8*** |
| 1000 | 210.4 ± 7.8*** | 213.3 ± 10.0*** |

21 DAYS ORAL DOSING
9-10 CHICKS PER GROUP (b) Intestinal Calcium Absorption in Chicks White Leghorn one-day-old cockerels are placed on the vitamin D-deficient diet and are housed under ultraviolet-free lighting for 21 days. Chicks are then used to determine the effects of test compounds on intestinal calcium absorption. A single oral dose of test compound dissolved in propylene glycol is administered. At various times after dosing, 2 $\mu$Ci of $^{45}$Ca (chloride) is given orally, and serum radioactivity is measured 45 minutes after administration of the isotope. Ten chicks are used in each treatment and control group and vehicle-treated controls are included at each time period. The results of the intestinal clacium absorption assay are shown in Table II. The results show that the S and R-epimers of $1,25,26(OH)_3D_3$ possess similar $^{45}$Ca intestinal absorption activity.

TABLE II

EFFECTS OF $1,25S,26(OH)_3D_3$ (COMPOUND A) AND $1,25R,26(OH)_3D_3$ (COMPOUND B) ON $^{45}$Ca ABSORPTION IN VITAMIN D-DEFICIENT CHICKS

| TREATMENT (ORAL) | TIME (HR) | NO. OF CHICKS | SERUM $^{45}$Ca CPM/0.2 ML |
|---|---|---|---|
| Vehicle, 0.2 ml | 3 | 10 | 1338 ± 51 |
| Compound A, 1 meg | | 10 | 1977 ± 122*** |
| Compound B, 1 meg | | 10 | 2077 ± 174*** |
| Vehicle, 0.2 ml | 6 | 10 | 1345 ± 89 |
| Compound A, 1 meg | | 10 | 2067 ± 128*** |
| Compound B, 1 meg | | 10 | 1992 ± 212* |
| Vehicle, 0.2 ml | 24 | 10 | 1002 ± 109 |
| Compound A, 1 meg | | 10 | 993 ± 80 NS |
| Compound B, 1 meg | | 10 | 1222 ± 110 NS |
| Vehicle, 0.2 ml | 48 | 10 | 1022 ± 77 |
| Compound A, 1 meg | | 10 | 1141 ± 87 NS |
| Compound B, 1 meg | | 10 | 1063 ± 70 NS |

(c) Prevention of EHDP-Induced Mineralization Block in Rats

Charles River CD male rats are treated for 10 consecutive days. The compound disodium ethane 1-hydroxy-1,1-diphosphonate (EHDP) is given subcutaneously on each treatment day at a dose of 2 mg 0.2 ml/rat in distilled water. Test compounds are administered orally on each treatment day in propylene glycol (0.2 m./rat). Rats are autopsied on the day after the last treatment day and tibias are processed by a modified von Kossa procedure based upon silver impregnation of bone salts. Epiphyseal plate widths are measured with a micrometer ocular using standard microscopic magnification (35×). Activity is based upon dose dependent narrowing of the widened epiphyseal plate induced by EHDP. Ten rats are used in each treatment group. Positive (EHDP alone) and negative (vehicles alone) control groups of ten rats each are included in each experiment. The results of the assay are shown in Table III. The results of this assay indicate that the 25R-epimer of $1,25,26(OH)_3D_3$ caused calcification of the tibial epiphipeal plate in EHDP-blocked rats while the 25S-epimer of $1,25,26(OH)_3D_3$ did not.

TABLE III

EFFECTS OF $1,25S,26(OH)_3D_3$ AND $1,25R,26(OH)_3D_3$ IN EHDP-TREATED RATS

| DOSE OF DRUG | MEAN TIBIA EPIPHYSEAL PLATE WIDTH (Micra) + S.E. | | |
|---|---|---|---|
| MCG/ RAT/DAY | EHDP + $1,25S,26(OH)_3D_3$ | EHDP Alone | EHDP + $1,25R,26(OH)_3D_3$ |
| 0 | | 1190 ± 42 | |
| 10 | 1162 ± 36 NS | | 611 ± 51*** |
| VEHICLE CONTROLS (NO EHDP) 376 ± 13 | | | |

10 DAYS ORAL DOSING
8 RATS PER GROUP (d) Effects of administering of $1,25S,26(OH)_3D_3$ and $1,25R,26(OH)_3D_3$ on serum levels of $1,25(OH)_3D_3$ and $25(OH)D_3$.

The effects of administration of 1,25S,26(OH)$_3$D$_3$ and 1,25R,26(OH)$_3$D$_3$ on serum levels of 1α,25(OH)$_2$D$_3$ and 25(OH)D$_3$ were determined according to the method of Mallen et al. Archives of Biochemistry and Biophysics, Vol. 201, No. 1, April 15, pp. 277–285, 1980. The results are shown in Table IV. The effect was initially shown in a 7 day experiment and later in a 28 day treatment study which demonstrated that the reduction of 1α,2-5(OH)$_2$D$_3$ levels was sustained. The ability to control endogenous production of 1α,25(OH)$_2$D$_3$ is clinically useful in the treatment of among other disease states, sarcoidosis and hypercalciuria.

TABLE IV

EFFECTS OF ADMINISTRATION OF 1,25S,26(OH)$_3$D$_3$ AND 1,25R,26(OH)$_3$D$_3$ ON SERUM LEVELS OF 1α25(OH)$_2$D$_3$ AND 25(OH)D$_3$

| TREATMENT DOSE/RAT/DAY, S.C. | NO. DAYS RX | NO. OF RATS | SERUM 1α,25(OH)$_3$D$_3$ PG/ML | 25(OH)D$_3$ NG/ML |
|---|---|---|---|---|
| Vehicle, 0.2 ml | 7 | 18 | 99.6 ± *.5 | 37.6 ± 1.9 |
| 1,25S,26(OH)$_3$D$_3$-1 meg | | 12 | 7.9 ± 2.8 | 32.0 ± 1.7 |
| 1,25R,26(OH)$_3$D$_3$-1 meg | | 12 | 24.0 ± 4.1 | 36.0 ± 1.8 |
| Vehicle, 0.2 ml | 28 | 10 | 32.8 ± 7.3 | 64.2 ± 4.3 |
| 1,25S,26(OH)$_3$D$_3$-1 meg | | 10 | 8.0 ± 2.3 | 40.6 ± 3.4 |
| 1,25R,26(OH)$_3$D$_3$-1 meg | | 10 | 8.2 ± 1.7 | 34.7 ± 4.2 |

The R and S epimers of the compound of formula I, suppress the serum levels of 1α,25(OH)$_2$D$_3$ when administered to a host suffering from disease states characterized by higher than normal levels of 1α,25(OH)$_2$D$_3$. The R and S epimers of formula I may be administered in dosages that are in the range of 0.5 micrograms to 500 micrograms per day. The R or S epimer is preferably administered orally, but they can also be administered subcutaneously, intramuscularly, intravenously, or intraperitoneally.

The R and S epimers of formula I can be administered to achieve the lowering of serum levels of 1α,2-5(OH)$_2$D$_3$ utilizing formulation, for example compositions such as tablets, capsules, and the like, or elixers for oral administration, or in sterile solutions or suspensions for parenteral administration. About 0.5 micrograms to 500 micrograms of an R or S epimer of formula I is compounded with a pharmaceutically acceptable vehicle, carrier, excipient, binder, preservative, stabilizer, flavor, and the like, in a unit dosage as called for by accepted pharmaceutical practice. The amount of active substance in the foregoing compositions or preparations is in the range previously indicated.

Illustrative of the adjuvants which may be incorporated into tablets, capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen, or cherry. Various other materials may be present as coatings or to otherwise modify the physical form of the dosage unit. For instance, tablets may be coated with shellac, sugar, or both. A syrup or elixer may contain the active compound, sucrose as a sweetening agent, methyl, and propyl parabens as preservatives, a dye, and a flavoring such as cherry or orange flavor.

Sterile compositions for injection can be formulated according to conventional pharmaceutical practice by dissolving or suspending the active substance in a vehicle, such as water for injection, a naturally-occurring vegetable oil, such as sesame oil, coconut oil, peanut oil, cottonseed oil, and the like, or a synthetic fatty vehicle such as ethyl oleate or the like. Buffers, preservatives, antioxidants and the like can be incorporated as required.

The Examples which follow further illustrate the invention. All temperatures are in degrees Centigrade unless otherwise stated.

EXAMPLE 1

A mixture of 0.91 g (0.0030 mole) of 1α,3β-dihydroxyandrost-5-en-17-one [R. M. Dodson, A. H. Goldkamp and R. D. Muir, J.Amer. Chem.Soc., 82, 4026 (1960)], 15 ml. of tetrahydrofuran, 1.26 g. (0.015 mole) of 3,4-dihydro-2H-pyran and 0.028 mg. of p-toluenesulfonic acid monohydrate was stirred at 25° for 18 hr. The mixture was diluted with methylene chloride. This solution was then washed with saturated aqueous sodium bicarbonate solution. The organic phase was dried over anhydrous magnesium sulfate, filtered and evaporated to dryness to yield oily [1α,3β]-1,3-bis-[(tetrahydro-2H-pyran-2-yl)oxy]androst-3-en-17-one, $[\alpha]_D^{20}$+34.3° (c 1, CHCl$_3$).

EXAMPLE 2

To a mixture of 1.00 g (0.0021 mole) of [1α,3β]-1,3-bis-[(tetrahydro-2H-pyran-2-yl)oxy]androst-3-en-17-one, 1.94 g. (0.0087 mole) of triethyl phosphonoacetate, and 14 ml. of ethyl alcohol was added 0.68 g. (0.010 mole) of sodium ethoxide in 7 ml. of ethanol. The mixture was stirred at reflux (80° C.) for 18 hr. and cooled. The mixture was concentrated under reduced pressure. The residue was partitioned between water and ether and the organic phase was washed with saturated brine. The organic phase was then dried over anhydrous magnesium sulfate, filtered and evaporated to dryness. The residue was chromatographed on 0.06–0.20 mm silica gel to yield [1α,3β,17(20)E]-1,3-bis-[(tetra-2H-pyran-2-yl)oxy]pregna-5,17(20)-dien-21-oic acid ethyl ester, $[\alpha]_D^{20}$−8° (c 1, CHCl$_3$).

EXAMPLE 3

A mixture of 0.32 g. (0.00059 mole) of [1α,3β,17(2-0)E]-1,3-bis[(tetrahydro-2H-pyran-2-yl)oxy]pregna-5,17(20)-dien-21-oic acid ethyl ester, 0.10 g of platinum oxide, and 20 ml. of ethanol was stirred in 1 atmosphere of hydrogen for 2 hr. The mixture was filtered through a pad of diatomaceous earth and the solids were washed with ethanol. The combined filtrates were evaporated to dryness to yield oily [1α,3β]-1,3-bis[(tetrahydro-2H-pyran-2-yl)-oxy]pregn-5-en-21-oic acid ethyl ester, $[\alpha]_D^{23}$−13° (c 1, CHCl$_3$).

EXAMPLE 4

To a solution of 8.0 ml. of diisopropylamine in 14 ml. of tetrahydrofuran at −30° C. was added 29.8 ml. (0.0477 mole) of 1.6M of butyllithium in hexane. After stirring for 0.5 hr, 20.0 g. (0.0367 mole) of [1α,3β]-1,3-bis[(tetrahydro-2H-pyran-2-yl)-oxy]pregn-5-en-21-oic acid ethyl ester in 180 ml. of tetrahydrofuran was added dropwise. The mixture was stirred for 1 hr at −30° C. and cooled to −70° C. A solution of 15.64 g. (0.0551 mole) of 5-iodo-2S-methylpentane-1,2-diol cyclic 1,2-(1-methylethylidene acetal) in 22 ml. of hexamethylphosphoramide was added dropwise. The mixture was stirred at −70° C. for 1 hr and was allowed to warm to 25° C. and stir for 1 hr. The mixture was then diluted with 9:1 hexane-ether. The solution was washed with water, and saturated brine. The organic phase was dried over anhydrous magnesium sulfate, filtered, and evaporated to dryness. The residue was purified by column chromatography on 0.06–0.20 mm silica gel to give [1α,3β,25S]-1,3-bis[(tetrahydro-2H-pyran-2-yl)oxy]-cholest-5-en-21-oic acid 25,26-diol cyclic (1-methylethylidene acetal) ethyl ester, $[\alpha]_D^{20}+6.7°$ (c 1, CHCl$_3$).

EXAMPLE 5

To a solution of 3.41 ml. of diisopropylamine in 6 ml. of tetrahydrofuran at −30° was added 12.6 ml. of 1.6M butyllithium in hexane. After stirring for 0.5 hr, 8.50 g. (0.0156 mole) of [1α,3β]-1,3-bis[(tetrahydro-2H-pyran-2-yl)oxy]pregn-5-en-21-oic acid ethyl ester in 77 ml. of tetrahydrofuran was added dropwise. The mixture was stirred for 1 hr at −30° C. and cooled to −70° C. A solution of 6.65 g. (0.0234 mole) of 5-iodo-2R-methyl-pentane-1,2-diol cyclic 1,2-(1-methylethylidene acetal) in 9 ml. of hexamethylphosphoramide was then added dropwise. The mixture was stirred at −70° C. for 1 hr and was allowed to warm to 25° C. and stir for 1 hr. The mixture was diluted with 9:1 hexane-ether. The solution was washed with water, and saturated brine. The organic phase was dried over anhydrous magnesium sulfate, filtered and evaporated to dryness. The residue was purified by column chromatography on 0.06–0.20 mm silica gel to give [1α,3β,25R]-1,3-bis[(tetrahydro-2H-pyran-2-yl)oxy]chlolest-5-en-21-oic acid 25,26-diol cyclic (1-methylethylidene acetal) ethyl ester, $[\alpha]_D^{20}+8.3°$ (c 1, CHCl$_3$).

EXAMPLE 6

To a mixture of 2.05 g. (0.0090 mole) of lithium aluminum hydride and 100 ml. of tetrahydrofuran at 0° C. was added 25.2 g. of [1α,3β,25S]-1,3-bis[(tetrahydro-2H-pyran-2-yl)oxy]cholest-5-en-21-oic acid 25,26-diol cyclic (1-methylethylidene acetal) ethyl ester in 250 ml. of tetrahydrofuran. The mixture was heated at 60° C. for 1.5 hr, recooled to 0° C., and diluted with 900 ml. of ether. The mixture was then quenched with the dropwise addition of 4.10 ml. of water and 3.30 ml. of 10% aqueous sodium hydroxide. The mixture was stirred at 25° C. for 1 hr. and was filtered. The solids were triturated with ether and filtered. Evaporation of solvent afforded [1α,3β,25S]-1,3-bis[(tetrahydro-2H-pyran-2-yl)oxy]cholest-5-en-21,25,26-triol cyclic 25,26-(1-methylethylidene acetal), $[\alpha]_D^{25}-4.6°$ (c 1, CHCl$_3$).

EXAMPLE 7

To a mixture of 0.853 g. (0.0225 mole) of lithium aluminum hydride in 42 ml. of tetrahydrofuran at 0° C. was added 10.5 g. (0.0150 mole) of [1α,3β,25R]-1,3-bis[-(tetrahydro-2H-pyran-2-yl)-oxy]cholest-5-en-21-oic acid 25,26-diol cyclic (1-methylethylidene acetal) ethyl ester in 100 ml. of tetrahydrofuran. The mixture was stirred at 60° C. for 1.5 hr, recooled to 0° C. and diluted with 380 ml. of ether. The mixture was then quenched with the dropwise addition of 1.62 ml. of water and 1.36 ml. of 10% aqueous sodium hydroxide. The mixture was stirred at 25° C. for 1 hr and was filtered. The solids were triturated with ether and filtered. Evaporation of solvent afforded [1α,3β,25R]-1,3-bis[(tetrahydro-2H-pyran-2-yl)oxy]cholest-5-en-21,25,26-triol cyclic 25,26-(1-methylethylidene acetal), $[\alpha]_D^{25}-0.6°$, (c 1, CHCl$_3$).

EXAMPLE 8

A mixture of 24.20 g. (0.0358 mole) of [1α,3β,25S]-1,3-bis[(tetrahydro-2H-pyran-2-yl)oxy]cholest-5-en-21,25,26-triol cyclic 25,26-(1-methylethylidene acetal), 150 ml. of pyridine and 13.52 g. (0.0708 mole) of p-toluenesulfonyl chloride was stirred at 0° C. for 18 hr. The mixture was quenched with ice chips. The mixture was then poured into water and extracted with methylene chloride. The organic phase was washed with 10% aqueous sulfuric acid and saturated aqueous sodium bicarbonate solution. The organic layer was dried over anhydrous magnesium sulfate, filtered and evaporated to dryness to yield oily [1α,3β,25S]-1,3-bis[(tetrahydro-2H-pyran-2-yl)oxy]cholest-5-en-21,25,26-triol cyclic 25,26-(1-methylethylidene acetal) 21-(4-methylbenzenesulfonate), $[\alpha]_D^{22}-3.7°$ (c 1, CHCl$_3$).

EXAMPLE 9

A mixture of 10.24 g. (0.0155 mole) of [1α,3β,25R]-1,3-bis[(tetrahydro-2H-pyran-2-yl)oxy]cholest-5-en-21,25,26-triol cyclic 25,26-(1-methylethylidene acetal), 63 ml. of pyridine and 5.94 g. (0.0311 mole) of p-toluenesulfonyl chloride was stirred at 0° C. for 18 hr. The mixture was quenched with ice chips. The mixture was then poured into water and extracted with methylene chloride. The organic phase was washed with 10% aqueous sulfuric acid and saturated aqueous sodium bicarbonate solution. The organic layer was dried over anhydrous magnesium sulfate, filtered, and evaporated to dryness to yield oily [1α,3β,25R]-1,3-bis[(tetrahydro-2H-pyran-2-yl)oxy]cholest-5-en-21,25,26-triol cyclic 25,26-(1-methylethylidene acetal) 21-(4-methylbenzenesulfonate), $[\alpha]_D^{23}+2.1°$ (c 1, CHCl$_3$).

EXAMPLE 10

A mixture of 0.081 g. (0.0001 mole) of [1α,3β,25S]-1,3-bis[(tetrahydro-2H-pyran-2-yl)oxy]cholest-5-en-21,25,26-triol cyclic 25,26-(1-methylethylidene acetal) 21-(4-methylbenzenesulfonate), and 0.150 g. (0.0010 mole) of sodium iodide in 2 ml. of acetone was heated at 50° for 18 hr and cooled. The mixture was poured into water and the product was isolated with methylene chloride. The organic layers were washed with aqueous sodium sulfite solution, and saturated aqueous sodium bicarbonate solution. The organic layers were dried over anhydrous magnesium sulfate, filtered and evaporated to dryness to yield [1α,3β,25S]1,3-bis[(tetrahydro-2H-pyran-2-yl)oxy]-21-iodocholest-5-en-25,26-diol cyclic 25,26-(1-methylethylidene acetal).

EXAMPLE 11

A mixture of 0.081 g. (0.0001 mole) of [1α,3β,25R]-1,3-bis[(tetrahydro-2H-pyran-2-yl)oxy]cholest-5-en-21,25,26-triol cyclic 25,26-(1-methylethylidene acetal) 21-(4-methylbenzenesulfonate), and 0.165 g. (0.0011 mole) of sodium iodide in 2 ml. of acetone was heated at 50° for 18 hr and cooled. The mixture was poured into water and the product was isolated with methylene chloride. The organic layers were washed with aqueous sodium sulfite solution, and saturated aqueous sodium bicarbonate solution. The organic layers were dried over anhydrous magnesium sulfate, filtered and evaporated to dryness to yield [1α,3β,25R]-1,3-bis[(tetrahydro-2H-pyran-2-yl)oxy]-21-iodocholest-5-en-25,26-diol cyclic 25,26-(1-methylethylidene acetal).

EXAMPLE 12

A. A mixture of 4.43 g. (0.1166 mole) of lithium aluminum hydride, 410 ml. of tetrahydrofuran and 31.60 g. (0.0357 mole) of [1α,3β,25S]-1,3-bis[(tetrahydro-2H-pyran-2-yl)oxy]cholest-5-en-21,25,26-triol cyclic 25,26-(1-methylethylidene acetal) 21-(4-methylbenzenesulfonate) was heated at reflux (60° C.) for 1 hr and cooled to 0° C. The mixture was diluted with 900 ml. of ether and quenched with the dropwise addition of 8.86 ml. of water and 7.09 ml. of 10% aqueous sodium hydroxide solution. The mixture was then stirred for 1 hr and filtered. The solids were triturated with ether and filtered. The combined filtrates were evaporated to dryness and chromatographed on 0.06–0.20 mm silica gel to yield [1α,3β,25S]-1,3-bis[(tetrahydro-2H-pyran-2-yl)oxy]cholest-5-en-25,26-diol cyclic 25,26-(1-methylethylidene acetal), $[\alpha]_D^{22} - 6.6°$ (c 1, CHCl$_3$).

B. By an alternative procedure, a mixture of 0.078 g. (0.0001 mole) of [1α,3β,25S]-1,3-bis[(tetrahydro-2H-pyran-2-yl)oxy]-21-iodocholest-5-en-25,26-diol cyclic 25,26-(1-methylethylidene acetal), 0.045 g. (0.00015 mole) of tri-n-butyltin hydride and 3 ml. of tetrahydrofuran were stirred at 25° C. for 18 hr under an argon atmosphere. The mixture was evaporated to dryness and the residue was purified by chromatography on 0.06–0.20 mm silica gel to yield [1α,3β,25S]-1,3-bis[(tetrahydro-2H-pyran-2-yl)oxy]cholest-5-en-25,26-diol cyclic 25,26-(1-methylethylidene acetal), $[\alpha]_D^{23} - 6.5°$ (c 1, CHCl$_3$).

EXAMPLE 13

A. A mixture of 1.93 g. (0.0509 mole) of lithium aluminum hydride, 180 ml. of tetrahydrofuran, and 13.46 g. (0.0166 mole) of [1α,3β,25R]-1,3-bis[(tetrahydro-2H-pyran-2-yl)oxy]cholest-5-en-21,25,26-triol cyclic 25,26-(1-methylethylidene acetal) 21-(4-methylbenzenesulfonate) was heated at reflux (60° C.) for 1 hr and cooled to 0° C. The mixture was diluted with 400 ml. of ether and quenched with the dropwise addition of 3.86 ml. of water and 3.10 ml. of 10% aqueous sodium hydroxide solution. The mixture was then stirred for 1 hr and filtered. The solids were triturated with ether and filtered. The combined filtrates were evaporated to dryness and chromatographed on 0.06–0.20 mm silica gel to yield [1α,3β,25R]-1,3-bis[(tetrahydro-2H-pyran-2-yl)oxy]cholest-5-en-25,26-diol cyclic 25,26-(1-methylethylidene acetal), $[\alpha]_D^{25} - 2.5°$ (c 1, CHCl$_3$).

B. By an alternative procedure, a mixture of 0.076 g. (0.0001 mole) of [1α,3β,25R]-1,3-bis[(tetrahydro-2H-pyran-2-yl)oxy]-21-iodocholest-5-en-25,26-diol cyclic 25,26-(1-methylethylidene acetal), 0.044 g. (0.00015 mole) of tri-n-butytin hydride and 3 ml of tetrahydrofuran were stirred at 25° C. for 18 hr under an argon atmosphere. The mixture was evaporated to dryness and the residue was purified by chromatography on 0.06–0.20 mm silica gel to yield [1α,3β,25R]-1,3-bis[(tetrahydro-2H-pyran-2-yl)oxy]cholest-5-en-25,26-diol cyclic 25,26-(1-methylethylidene acetal), $[\alpha]_D^{25} - 2.5°$ (c 1, CHCl$_3$).

EXAMPLE 14

A mixture of 24.71 g. (0.0355 mole) of [1α,3β,25S]-1,3-bis-[(tetrahydro-2H-pyran-2-yl)oxy]cholest-5-en-25,26-diol cyclic 25,26-(1-methylethylidene acetal), 420 ml. of methanol, 420 ml. of 2,2-dimethoxypropane and 4.20 g. of p-toluenesulfonic acid monohydrate was stirred at 25° C. for 5 hr. The mixture was quenched by adding 40 ml. of saturated aqueous sodium bicarbonate solution and stirring for 0.5 hr. The mixture was then evaporated to dryness. The residue was triturated with ethyl acetate, filtered, and evaporated to dryness. The crude solid was purified by chromatography on 0.06–0.20 mm silica gel to yield [1α,3β,25S]-cholest-5-en-1,3,25,26-tetrol cyclic 25,26-(1-methylethylidene acetal), m.p. 175°–177°, $[\alpha]_D^{21} - 39.9°$ (c 1, CHCl$_3$).

EXAMPLE 15

A mixture of 10.65 g. (0.0165 mole) of [1α,3β,25R]-1,3-bis[(tetrahydro-2H-pyran-2-yl)oxy]cholest-5-en-25,26-diol cyclic 25,26-(1-methylethylidene acetal), 180 ml. of methanol, 180 ml. of 2,2-dimethoxypropane, and 1.80 g. of p-toluenesulfonic acid monohydrate was stirred at 25° for 5 hr. The mixture was quenched with 20 ml. of saturated aqueous sodium bicarbonate solution and stirring for 0.5 hr. The mixture was evaporated to dryness. The residue was purified by chromatography on 0.06–0.20 mm silica gel to yield [1α,3β,25R]-cholest-5-en-1,3,25,26-tetrol cyclic 25,26-(1-methylethylidene acetal), m.p. 151°–153°, $[\alpha]_D^{25} - 27.9°$ (c 1, CHCl$_3$).

EXAMPLE 16

A mixture of 10.93 g. (0.0230 mole) of [1α,3β,25S]-cholest-5-1,3,25,26-tetrol cyclic 25,26-(1-methylethylidene acetal), 82 ml. of pyridine, 21 ml. of acetic anhydride and 1.09 g. of 4-dimethylaminopyridine were stirred at 0° C. for 1 hr and at 25° for 24 hr. The mixture was diluted with 20 ml. of methanol at 0° C. and evaporated to dryness. The residue was then dissolved in methylene chloride. This solution was washed with 10% aqueous sulfuric acid and saturated sodium bicarbonate solution. The organic phase was dried over anhydrous magnesium sulfate, filtered, and evaporated to dryness to yield [1α,3β,25S]-cholest-5-en-1,3,25,26-tetrol cyclic 25,26-(1-methylethylidene acetal) 1,3-diacetate, $[\alpha]_D^{21} - 19.0°$ (c 1, CHCl$_3$).

EXAMPLE 17

A mixture of 4.58 g. (0.0097 mole) of [1α,3β,25R]-cholest-5-en-1,3,25,26-tetrol cyclic 25,26-(1-methylethylidene acetal), 34 ml. of pyridine, 8.8 ml. of acetic anhydride, and 0.45 g. of 4-dimethylaminopyridine was stirred at 0° C. for 1 hr and at 25° C. for 2 hr. The mixture was diluted with 10 ml. of methanol at 0° C. and evaporated to dryness. The residue was then dissolved in methylene chloride. This solution was washed with 10% aqueous sulfuric acid and saturated sodium bicarbonate solution. The organic phase was dried over anhydrous magnesium sulfate, filtered, and evaporated to dryness to yield [1α,3β,25R]-cholest-5-en-1,3,25,26-tetrol cyclic 25,26-(1-methylethylidene acetal) 1,3-diacetate, $[\alpha]_D^{20} - 14.4°$ (c 1, CHCl$_3$).

EXAMPLE 18

A mixture of 12.79 g. (0.0228 mole) of [1α,3β,25S]-cholest-5-en-1,3,25,26-tetrol cyclic 25,26-(1-methylethylidene acetal) 1,3-diacetate, 10.31 g. of sodium bicarbonate, 4.38 g. (0.0150 mole) of 1,3-dibromo-5,5-dimethylhydantoin and 500 ml. of hexane was heated at reflux (80° C.) for 1 hr and cooled. The mixture was filtered and the solids were triturated with hexane and filtered. The filtrates were evaporated to dryness to yield [1α,3β,25S]-7-bromocholest-5-en-1,3,25,26-tetrol cyclic 25,26-(1-methylethylidene acetal) 1,3-diacetate.

EXAMPLE 19

A mixture of 5.35 g. (0.0096 mole) of [1α,3β,25R]-cholest-5-ene-1,3,25,26-tetrol cyclic 25,26-(1-methylethylidene acetal) 1,3-diacetate, 4.34 g. of sodium bicarbonate, 1.84 g. (0.00630 mole) of 1,3-dibromo-5,5-dimethylhydantoin, and 210 ml. of hexane was heated at reflux (80° C.) for 1 hr and cooled. The mixture was filtered and the solids were triturated with hexane and filtered. The combined filtrates were evaporated to dryness to yield [1α,3β,25R]-7-bromocholest-5-en-1,3,25,26-tetrol cyclic 25,26-(1-methylethylidene acetal) 1,3-diacetate.

EXAMPLE 20

A mixture of 13.2 g. (0.0228 mole) of crude [1α,3β,25S]-7-bromocholest-5-en-1,3,25,26-tetrol cyclic 25,26-(1-methylethylidene acetal) 1,3-diacetate, 9.37 ml. of s-collidine and 120 ml. of xylene was heated at reflux (140° C.) for 1.5 hr and cooled. The mixture was diluted with 350 ml. of hexane. This solution was washed with 10% aqueous sulfuric acid, and saturated aqueous sodium bicarbonate solution. The organic phase was dried over anhydrous magnesium sulfate, filtered, and evaporated to dryness. The residue was purified by column chromatography on 0.06–0.20 mm silica gel to yield [1α,3β,25S]-cholesta-5,7-diene-1,3,25,26-tetrol cyclic 25,26-(1-methylethylidene acetal) 1,3-diacetate, m.p. 105°–107°, $[\alpha]_D^{24}$ −27.9° (c 1, CHCl$_3$).

EXAMPLE 21

A mixture of 6.00 g. (0.0096 mole) of crude [1α,3β,25R]-7-bromocholest-5-en-1,3,25,26-tetrol cyclic 25,26-(1-methylethylidene acetal) 1,3-diacetate, 3.9 ml. of a s-collidine and 105 ml. of xylene was heated at reflux (140° C.) for 1.5 hr and cooled. The mixture was diluted with 150 ml of hexane. This solution was washed with 10% aqueous sulfuric acid, and saturated sodium bicarbonate solution. The organic phase was dried over anhydrous magnesium sulfate, filtered, and evaporated to dryness. The residue was purified by column chromatography on 0.06°–0.20 mm silica gel to yield [1α,3β,25R]-cholesta-5,7-diene-1,3,25,26-tetrol cyclic 25,26-(1-methylethylidene acetal) 1,3-diacetate, $[\alpha]_D^{20}$ −24.9° (c 1, CHCl$_3$).

EXAMPLE 22

A mixture of 1.74 g. (0.0031 mole) of [1α,3β,25S]-cholesta-5,7-diene-1,3,25,26-tetrol cyclic 25,26-(1-methylethylidene acetal) 1,3-diacetate in 600 ml. of hexane and 200 ml. of tetrahydrofuran was irradiated for 1 hr under argon at −5° C. using a 450W Hanovia high pressure mercury lamp, cooled with a Vycor-glass cooling finger. The solution was evaporated to dryness and the residue was purified with a Waters Associates liquid chromatograph Model 202 using 4'×1" silica gel column and a 7:1 mixture of n-hexane-ethyl acetate as eluant to give [1α,3β,6Z,25S]-9,10-secocholesta-5(10),6,8-triene-1,3,25,26-tetrol cyclic 25,26-(1-methylethylidene acetal) 1,3-diacetate, $[\alpha]_D^{23}$ −52.2° (c 0.5, CHCl$_3$).

EXAMPLE 23

A mixture of 1.90 g. (0.0034 mole) of [1α,3β,25R]-cholesta-5,7-diene-1,3,25,26-tetrol cyclic 25,26-(1-methylethylidene acetal) 1,3-diacetate in 800 ml. of 3:1 hexane-tetrahydrofuran was irradiated for 2 hr under argon at −5° C. using a 450W Hanovia high pressure mercury lamp, cooled with a Vycor-glass cooling finger. The solution was evaporated to dryness and the residue was purified with a Waters Associates liquid chromatograph Model 202 using a 4'×1" silica gel column and a 7:1 mixture of n-hexane-ethyl acetate as eluant to give [1α,3β,6Z,25R]-9,10-secocholesta-5(10),6,8-triene-1,3,25,26-tetrol cyclic 25,26-(1-methylethylidene acetal) 1,3-diacetate, $[\alpha]_D^{20}$ −52.0° (c 1, CHCl$_3$).

EXAMPLE 24

A solution of 0.443 g. (0.0080 mole) of [1α,3β,6Z,25S]-9,10-secocholesta-5(10),6,8-triene-1,3,25,26-tetrol cyclic 25,26-(1-methylethylidene acetal) 1,3-diacetate, and 15 ml. of 1.5% of potassium hydroxide in methanol was stirred at 0° C. for 17 hr. The mixture was neutralized to pH 7.5 with glacial acetic acid in methanol. The solution was then evaporated to dryness at 2° C. The residue was partitioned between ethyl acetate and water. The organic phase was washed with saturated brine and dried over anhydrous sodium sulfate. The mixture was filtered and evaporated to dryness to yield [1α,3β,6Z,25S]-9,10-secocholesta-5(10),6,8-triene-1,3,25,26-tetrol cyclic 25,26-(1-methylethylidene acetal).

EXAMPLE 25

A mixture of 0.515 g. (0.00093 mole) of [1α,3β,6Z,25R]-9,10-secocholesta-5(10),6,8-triene-1,3,25,26-tetrol cyclic 25,26-(1-methylethylidene acetal) 1,3-diacetate, and 20 ml. of 1.5% of potassium hydroxide in methanol was stirred at 0° C. for 17 hr. The mixture was neutralized to pH 7.5 with glacial acetic acid in methanol. The solution was then evaporated to dryness at 0° C. The residue was partitioned between ethyl acetate and water. The organic phase was washed with saturated brine and dried over anhydrous sodium sulfate. The mixture was filtered and evaporated to dryness to yield [1α,3β,6Z,25R]-9,10-secocholesta-5(10),6,8-triene-1,3,25,26-tetrol cyclic 25,26-(1-methylethylidene acetal).

EXAMPLE 26

A mixture of 0.174 g. (0.0003 mole) of [1α,3β,6Z,25S]-9,10-secocholesta-5(10),6,8-triene-1,3,25,26-tetrol cyclic 25S,26-(1-methylethylidene acetal) and 5 ml. of p-dioxane was heated at reflux (100° C.) for 1 hr and cooled. The mixture was then evaporated to dryness. The residue was purified with a Waters Associates liquid chromatograph Model 202 using a 4'×1" silica gel column and 3:1 ethyl acetate-hexane as eluant to give [1α,3β,5Z,7E,25S]-9,10-secocholesta-5,7,10(19)-triene-1,3,25,26-tetrol cyclic 25,26-(1-methylethylidene acetal), $[\alpha]_D^{23}$ +26.9° (c 0.5, CHCl$_3$).

EXAMPLE 27

A mixture of 0.440 g. (0.0009 mole) of [1α,3β,6Z,25R]-9,10-secocholesta-5(10),6,8-triene-1,3,25,26-tetrol cyclic 25,26-(1-methylethylidene acetal) and 15 ml. of dioxane was heated at reflux (100° C.) for 1 hr and cooled. The mixture was then evaporated to dryness. The residue was purified on a Waters Associates liquid chromatograph Model 202 using a 4'×1" silica gel column and 3:1 ethyl acetate-hexane as eluant to give [1α,3β,5Z,7E,25R]-9,10-secocholesta-5,7,10(19)-triene-1,3,25,26-tetrol cyclic 25,26-(1-methylethylidene acetal) $[60]_D^{20}$ +28.4° (c 0.5, CHCl$_3$).

EXAMPLE 28

A mixture of 0.222 g. (0.0005 mole) of [1α,3β,5Z,7E,25S]-9,10-secocholesta-5,7,10(19)-triene-1,3,25,26-tetrol cyclic 25,26-(1-methylethylidene acetal), 0.500 g. of the hydrogen form of a cation exchange resin (Bio-Rad AG 50W-X4), and 37 ml. of methanol was stirred under argon at 20° C. for 22 hr. The reaction mixture was then filtered and the filtrate was evaporated to dryness. The residue was purified on a Waters Associates liquid chromatograph Model 202 using a 4'×1" silica gel column and ethyl acetate as eluant to give [1α,3β,5Z,7E,25S]-9,10-secocholesta-5,7,10(19)-triene-1,3,25,26-tetrol also known as 1α,25S,26-trihydroxy-cholecalciferol, mp 162°–164°, $[\alpha]_D^{23} + 58.8°$ (c 0.5, CH$_3$OH).

EXAMPLE 29

A mixture of 0.319 g. (0.0007 mole) of [1α,3β,5Z,7E,25R]-9,10-secocholesta-5,7,10(19)-triene-1,3,25,26-tetrol cyclic 25,26-(1-methylethylidene acetal), 0.718 g. of the hydrogen form of a cation exchange resin (Bio-Rad AG 50W-X4), and 37 ml. of methanol was stirred under argon at 20° C. for 22 hr. The reaction mixture was then filtered and the filtrate was evaporated to dryness. The residue was purified on a Waters Associates liquid chromatograph Model 202 using a 4'×1" silica gel column and ethyl acetate as eluant to give [1α,3β,5Z,7E,25R]-9,10-secocholesta-5,7,10(19)-triene-1,3,25,26-tetrol also known as 1α,25R,26-trihydroxy-cholecalciferol, m.p. 146°–148° $[\alpha]_D^{21} + 63.8°$ (c 0.5, CH$_3$OH).

EXAMPLE 30

Tablet Formulation

| | mg/tablet | | |
|---|---|---|---|
| 1. 1,25S,26 trihydroxy-cholecalciferol | 0.025 | 0.100 | 0.5 |
| 2. Lactose | 157.975 | 157.900 | 157.5 |
| 3. Avicel PH 102* | 20.000 | 20.00 | 20.0 |
| 4. Modified Starch | 20.000 | 20.000 | 20.0 |
| 5. Magnesium Stearate | 2.000 | 2.000 | 2.0 |
| Total | 200.000 mg | 200.000 mg | 200.0 mg |

*Microcrystalline Cellulose

Procedure:
1. Mix items 1–4 in a suitable mixer; mill if necessary.
2. Add magnesium stearate and mill.
3. Compress on suitable press.

EXAMPLE 31

Capsule Formulation

| | mg/capsule | | |
|---|---|---|---|
| 1. 1,25S,26 trihydroxy-cholecalciferol | 0.025 | 0.100 | 0.500 |
| 2. Lactose | 155.975 | 159.90 | 159.50 |
| 3. Modified Starch | 20.0 | 20.0 | 20.0 |
| 4. Talc | 20.0 | 20.0 | 20.0 |
| Total | 200 mg | 200 mg | 200 mg |

Procedure:
1. Dissolve Item 1 in alcohol.
2. Mix Items 2 and 3; solution in Step 1 is spread over the mixture. Dry overnight.
3. Screen the drug mixture Mix with talc.
4. Fill into capsules.

The drug can be dissolved in pharmaceutically acceptable solvents such as alcohol, propylene glycol, glycerine, polyethylene glycol. Surfactants, such as polyethylene glycol sorbitan esters, dioctyl sodium sulfosuccinate, polyoxyethylenepolyoxy propylene copolymer can also be added for solubilization of drug. The preservative also can be added to the formulation for the prevention of microbial growths. Illustrative of such formulations are:

| | mg/capsule | | |
|---|---|---|---|
| 1. 1,25S,26 trihydroxy-cholecalciferol | 0.025 | 0.1 | 0.50 |
| Polyethylene Glycol | 400.0 | 400.0 | 400.0 |
| Butylated Hydroxyanisole | 0.2 | 0.2 | 0.2 |
| Ascorbyl Palmitate | 1.0 | 1.0 | 1.0 |

Dissolve BHA and ascorbyl palmitate in PEG 400. Add 1,25S,26 trihydroxycholecalciferol and dissolve under an atmosphere of nitrogen. The liquid is filled into soft-shell capsules.

| | mg/capsule | | |
|---|---|---|---|
| 2. 1,25S,26 trihydroxy-cholecalciferol | 0.025 | 0.1 | 0.50 |
| Polyethylene Glycol 400 | 200.0 | 200.0 | 200.0 |
| Polysorbate 80* | 200.0 | 200.0 | 200.0 |
| Butylated Hydroxyanisole | 0.2 | 0.2 | 0.2 |
| Ascorbyl Palmitate | 1.0 | 1.0 | 1.0 |
| 3. 1,25S,26 trihydroxy-cholecalciferol | 0.025 | 0.1 | 0.50 |
| Polyethylene Glycol 6000 | 200.0 | 200.0 | 200.0 |
| Polysorbate 60** | 200.0 | 200.0 | 200.0 |
| Butylated Hydroxyanisole | 0.2 | 0.2 | 0.2 |
| Ascorbyl Palmitate | 1.0 | 1.0 | 1.0 |

*Polyoxyethylene 20 Sorbitan Monooleate
**Polyoxyethylene 20 Sorbitan Monostearate Warm the mixture of PEG 6000 and Polysorbate 60. Add to it BHA and ascorbyl palmitate. Add 1,25S,26 trihydroxy-cholecalciferol under an atomosphere of nitrogen. Fill into hard-shell capsules.

| | mg/capsule | | |
|---|---|---|---|
| 4. 1,25S,26 trihydroxy-cholecalciferol | 0.025 | 0.1 | 0.50 |
| Polyethylene Glycol 400 | 100.0 | 100.0 | 100.0 |
| Polyethylene Glycol 4000 | 300.0 | 300.0 | 300.0 |
| Butylated Hydroxyanisole | 0.1 | 0.1 | 0.1 |
| Butylated Hydroxytoluene | 0.1 | 0.1 | 0.1 |
| Ascorbyl Palmitate | 1.0 | 1.0 | 1.0 |

Warm a mixture of PEG 400 and PEG 4000. Add BHT and ascorbyl palmitate, dissolve. Add 1,25S,26 trihydroxy-cholecalciferol and dissolve under a stream of nitrogen. Fill into hard-shell capsules.

EXAMPLE 32

Tablet Formulation

| | mg/tablet | | |
|---|---|---|---|
| 1. 1,25R,26-trihydroxy-cholecalciferol | 0.025 | 0.100 | 0.5 |
| 2. Lactose | 157.975 | 157.900 | 157.5 |
| 3. Avicel PH 102 | 20.000 | 20.000 | 20.0 |
| 4. Modified Starch | 20.000 | 20.000 | 20.0 |
| 5. Magnesium Stearate | 2.000 | 2.000 | 2.0 |
| Total | 200.000 mg | 200.000 mg | 200.0 mg |

Procedure:
1. Mix items 1–4 in a suitable mixer; mill if necessary.
2. Add magnesium stearate and mill.

3. Compress on suitable press.

EXAMPLE 33

Capsule Formulation

|   |   | mg/capsule | | |
|---|---|---|---|---|
| 1. | 1,25R,26-trihydroxy-cholecalciferol | 0.025 | 0.100 | 0.500 |
| 2. | Lactose | 155.975 | 159.90 | 159.50 |
| 3. | Modified Starch | 20.0 | 20.0 | 20.0 |
| 4. | Talc | 20.0 | 20.0 | 20.0 |
|   | Total | 200 mg | 200 mg | 200 mg |

Procedure:
1. Dissolve Item 1 in alcohol.
2. Mix Items 2 and 3; solution in Step 1 is spread over the mixture. Dry overnight.
3. Screen the drug mixture. Mix with talc.
4. Fill into capsules.

The drug can be dissolved in pharmaceutically acceptable solvents such as alcohol, propylene glycol, glycerine, polyethylene glycol. Surfactants, such as polyethylene glycol sorbitan esters, dioctyl sodium sulfosuccinate, polyoxyethylenepolyoxy propylene copolymer can also be added for solubilization of drug. The preservative also can be added to the formulation for the prevention of microbial growths. Illustrative of such formulations are:

Typical Samples

|   |   | mg/capsule | | |
|---|---|---|---|---|
| 1. | 1,25R,26-trihydroxy-cholecalciferol | 0.025 | 0.1 | 0.50 |
|   | Polyethylene Glycol 400 | 400 | 400.0 | 400.00 |
|   | Butylated Hydroxyanisole | 0.2 | 0.2 | 0.2 |
|   | Ascorbyl Palmitate | 1.0 | 1.0 | 1.0 |

Dissolve BHA and ascorbyl palmitate in PEG 400. Add 1, 25 R,26-trihydroxycholecalciferol atmosphere of nitrogen. The liquid is filled into soft-shell capsules.

|   |   | mg/capsule | | |
|---|---|---|---|---|
| 2. | 1,25R,26-trihydroxy-cholecalciferol | 0.025 | 0.1 | 0.50 |
|   | Polyethylene Glycol 400 | 200 | 200.0 | 200.0 |
|   | Polyscorbate 80 | 200 | 200.0 | 200.0 |
|   | Butylated Hydroxyanisole | 0.2 | 0.2 | 0.2 |
|   | Ascorbyl Palmitate | 1.0 | 1.0 | 1.0 |
| 3. | 1,25R,26-trihydroxy-cholecalciferol | 0.025 | 0.1 | 0.50 |
|   | Polyethylene Glycol 6000 | 200 | 200.0 | 200.0 |
|   | Polyscorbate 60 | 200 | 200.0 | 200.0 |
|   | Butylated Hydroxyanisole | 0.2 | 0.2 | 0.2 |
|   | Ascorbyl Palmitate | 1.0 | 1.0 | 1.0 |

Warm the mixture of PEG 600 and Polysorbate 60. Add to it BHA and ascorbyl palmitate. Add 1,25R,26-trihydroxycholecalciferol under an atmosphere of nitrogen. Fill into hard-shell capsules.

|   |   | mg/capsule | | |
|---|---|---|---|---|
| 4. | 1,25R,26-trihydroxy-cholecalciferol | 0.025 | 0.1 | 0.50 |
|   | Polyethylene Glycol 400 | 100 | 100.0 | 100.0 |
|   | Polyethylene Glycol 4000 | 300 | 300.0 | 300.0 |
|   | Butylated Hydroxyanisole | 0.1 | 0.1 | 0.1 |
|   | Butylated Hydroxytoluene | 0.1 | 0.1 | 0.1 |
|   | Ascorbyl Palmitate | 1.0 | 1.0 | 1.0 |

Warm a mixture of PEG 400 and PEG 4000. Add BHT and ascorbyl palmitate, dissolve. Add 1,25R,26-trihydroxycholecalciferol and dissolve under a stream of nitrogen. Fill into hard-shell capsules.

What is claimed:

1. A method for the treatment of disease states characterized by higher than normal serum levels of endogenously produced 1α,25 dihydroxycholecalciferol which comprises administering to a host suffering from said disease states an effective amount of the C-25 R or S epimer of 1α,25, 26 trihydroxycholecalciferol.

2. The method of claim 1 wherein said disease states are selected from the group consisting of hypercalcemia, sarcoidosis, hypercalciuria, nephrolithiasis, and nephrocalcinosis.

3. The method of claim 2 wherein said effective amount of C-25 R or S epimer of 1α,25, 26 trihydroxycholecalciferol is in the range of from 5 to 500 micrograms per day.

4. The method of claim 3 wherein said host is a warm blooded animal.

5. The method of claim 4 wherein said C-25 epimer of 1α, 25, 26 trihydroxycholecalciferol is the C-25 S epimer.

6. The method of claim 4 wherein said C-25 epimer of 1α, 25, 26 trihydroxycholecalciferol is the C-25 R epimer.

7. A method for the treatment of disease states characterized by conditions wherein there is an increased sensitivity to 1α, 25-dihydroxy cholecalciferol which comprises administering to a host suffering from said disease states an effective amount of the C-25 R or S epimer of 1α,25, 26 trihydroxycholecalciferol.

8. The method of claim 7 wherein said C-25 R or S epimer of 1α, 25, 26-trihydroxycholecalciferol is administered in dosages in the range of from 5 to 500 micrograms per day.

9. The method of claim 8 wherein said C-25 epimer of 1α, 25, 26 trihydroxycholecalciferol is the C-25 S epimer.

10. The method of claim 8 wherein said C-25 epimer of 1α, 25, 26 trihydroxycholecalciferol is the C-25 R epimer.

11. The method of claim 5 wherein said disease state is hypercalcemia.

12. The method of claim 6 wherein said disease state is hypercalciuria.

* * * * *